(12) United States Patent
Eells et al.

(10) Patent No.: US 9,770,320 B2
(45) Date of Patent: Sep. 26, 2017

(54) STENT GRAFT REPAIR DEVICE

(75) Inventors: Scott E. Eells, Bloomington, IN (US); Thomas A. Osborne, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 1245 days.

(21) Appl. No.: 11/578,284

(22) PCT Filed: Apr. 12, 2005

(86) PCT No.: PCT/US2005/012310
§ 371 (c)(1),
(2), (4) Date: Oct. 12, 2006

(87) PCT Pub. No.: WO2005/099627
PCT Pub. Date: Oct. 27, 2005

(65) Prior Publication Data
US 2007/0219620 A1    Sep. 20, 2007

Related U.S. Application Data

(60) Provisional application No. 60/561,342, filed on Apr. 12, 2004.

(51) Int. Cl.
*A61F 2/06* (2013.01)
*A61F 2/07* (2013.01)
(Continued)

(52) U.S. Cl.
CPC ............... *A61F 2/07* (2013.01); *A61F 2/848* (2013.01); *A61F 2/89* (2013.01);
(Continued)

(58) Field of Classification Search
CPC ...... A61F 2/07; A61F 2/848; A61F 2002/826; A61F 2002/8483; A61F 2002/8486
(Continued)

(56) References Cited

U.S. PATENT DOCUMENTS 5,662,700 A * 9/1997 Lazarus ................. 606/194
6,344,056 B1    2/2002 Dehdashtian
(Continued)

FOREIGN PATENT DOCUMENTS

WO    WO 2004/002370 A1    1/2004
WO    WO 2004/017866 A1    3/2004

OTHER PUBLICATIONS

Examination Report for European Application No. 05734203.2 dated Jan. 27, 2017, 8 pages.

*Primary Examiner* — Brian Dukert
(74) *Attorney, Agent, or Firm* — Brinks Gilson & Lione

(57) ABSTRACT

A repair device (10) for affixing a migrating stent graft (30) to the interior surface of a vessel wall (31). The repair device includes tubular graft (11) with a bare or uncovered stent (16) affixed to the proximal end (12). The bare stent includes a plurality of distally pointed barbs (17) for securing the repair device to a vessel wall. A second stent (15) is positioned in the passage (14) of the tubular graft to expand the graft against the interior surface of the migrating stent graft (30). Proximally pointing barbs (20) are affixed to the struts of the second stent and extend through the graft material for securing the repair device to the migrating stent graft. Biological glue (22) and other sealing material (23) can be applied to the tubular graft and/or stents for sealing the repair device against the vessel wall and/or the interior of the migrating stent graft.

17 Claims, 5 Drawing Sheets

(51) Int. Cl.
*A61F 2/82* (2013.01)
*A61F 2/848* (2013.01)
*A61F 2/89* (2013.01)

(52) U.S. Cl.
CPC ... *A61F 2002/061* (2013.01); *A61F 2002/065* (2013.01); *A61F 2002/067* (2013.01); *A61F 2002/072* (2013.01); *A61F 2002/075* (2013.01); *A61F 2002/826* (2013.01); *A61F 2002/8483* (2013.01); *A61F 2002/8486* (2013.01); *A61F 2220/0008* (2013.01); *A61F 2220/0016* (2013.01); *A61F 2220/0075* (2013.01); *A61F 2230/005* (2013.01); *A61F 2230/0013* (2013.01); *A61F 2230/0054* (2013.01); *A61F 2230/0067* (2013.01); *A61F 2250/0069* (2013.01)

(58) Field of Classification Search
USPC ...................................... 623/1.13, 1.36, 1.14
See application file for complete search history.

(56) References Cited

U.S. PATENT DOCUMENTS

| | | | |
|---|---|---|---|
| 6,355,056 B1 * | 3/2002 | Pinheiro | 623/1.13 |
| 6,451,051 B2 * | 9/2002 | Drasler et al. | 623/1.15 |
| 6,517,573 B1 * | 2/2003 | Pollock et al. | 623/1.15 |
| 6,773,454 B2 | 8/2004 | Wholey et al. | 623/1.15 |
| 2001/0037142 A1 | 11/2001 | Stelter et al. | |
| 2001/0047198 A1 * | 11/2001 | Drasler et al. | 623/1.13 |
| 2003/0120263 A1 | 6/2003 | Ouriel et al. | |
| 2003/0158595 A1 * | 8/2003 | Randall et al. | 623/1.13 |
| 2003/0199967 A1 * | 10/2003 | Hartley et al. | 623/1.13 |
| 2003/0204242 A1 * | 10/2003 | Zarins et al. | 623/1.16 |
| 2003/0204249 A1 * | 10/2003 | Letort | 623/1.35 |
| 2003/0220683 A1 | 11/2003 | Minasian et al. | |
| 2004/0082989 A1 * | 4/2004 | Cook et al. | 623/1.13 |
| 2004/0098097 A1 * | 5/2004 | Fogarty et al. | 623/1.13 |
| 2004/0176833 A1 * | 9/2004 | Pavcnik et al. | 623/1.13 |

* cited by examiner

STENT GRAFT REPAIR DEVICE

TECHNICAL FIELD

This invention relates to medical devices and, in particular, to stent grafts. More specifically the invention is directed to a repair device for correcting leakage at the proximal (inflow) end of a stent graft due to migration or changes in the aneurysm that result in blood pressure being restored to the aneurysm sack, which could cause it to rupture.

BACKGROUND OF THE INVENTION

In many cases of abdominal aortic aneurysm (AAA), the diseased or weakened portion of the artery is near or up to the origins of the renal arteries. In these cases, it is difficult to get firm anchoring of the proximal end of an AAA stent graft. If the top stent of the stent graft cannot anchor to several millimeters of healthy tissue, there is a likelihood that there will be leakage around the top of the stent graft and/or migration of the stent graft out of the anchor area or "neck", resulting in even more leakage and the failure of the stent graft to protect the aneurysm from arterial blood pressure.

In these cases, the common method for repair has been to add a short stent graft extension to the top of the main stent graft to extend the length of the top portion of the main stent graft back into the neck of the aneurysm, just below the renal arteries. The problem with this approach is that since the neck of the artery is short, these extension devices do not create a good reliable seal in the neck and are still subject to migration. Also, since there are so many different brands and sizes of stent grafts, it is difficult to provide a standard set of extension stent grafts that can be kept on hand, ready to use when the migration occurs. As soon as the leakage to the aneurysm resumes, the danger of rupture is immediate. There is little or no time to fabricate, sterilize and ship a custom manufactured product. In addition, if the extension stent graft is placed more proximal, up into the aorta, the extension stent graft will occlude one or both of the renal arteries, causing a failure of one or both kidneys. Since most of the stent graft patients are not good open surgery candidates, complete surgical replacement of the diseased abdominal aorta, the only other method of repair for a migrating stent graft, is not a good option.

SUMMARY OF THE INVENTION

The foregoing problems are solved and a technical advance is achieved in an illustrative embodiment of a stent graft repair device of the present invention. The repair device includes a covered stent graft, which is somewhat similar to prior art extension devices, and, in addition, the proximal or top stent of the repair device advantageously includes a bare or non-covered stent with anchoring barbs that can be placed across, for example, the origins of the renal arteries without occluding them. This provides the advantage of being able to deploy the barbed, bare stent in an area of healthy artery wall where a good, secure anchor can be made without blocking or occluding the arteries. The barbed, top or bare stent advantageously prevents the possibility of further migration. The repair device of the present invention makes it possible to add the barbed top stent to implanted stent graft bodies of other manufacturers who do not use a barbed, bare top stent for anchoring. The repair device of this invention can also be used with stent grafts with barbed, bare top stents, like the ZENITH® AAA stent graft, available from Cook Incorporated, Bloomington, Ind., if it is needed to control a leak, or it is desired to extend the proximal end of the stent graft to a point closer to the origin of the renal arteries.

The stent graft repair device of this invention can be advantageously designed dimensionally so that only a total of about 12 different repair devices can practically accommodate all needs. This makes it practical for a hospital to stock all sizes so that the appropriate stent graft repair device is available at all times. This is especially important since a leaking stent graft poses an immediate threat to the patient and must be fixed as soon as possible. The repair device of this invention advantageously can be manufactured in two lengths (one or two stents in the passage of the graft and one top bare stent) and about 6 diameters for each length (from 15 to 35 mm diameter).

The stent graft repair device of this invention can also include barbs on the distal portion to improve the tensile strength of the connection between the repair device and the migrating stent graft body. The barbs on the distal end of the stent graft repair device protrude through the graft material from the internal stent and engage the graft material of the stent graft body. The barbs on the distal end can also be designed so that in a folded or compressed condition, as when the stent is in a delivery sheath, ready for delivery, the points or tips point inwardly, away from the wall of the delivery sheath so as to not scrape or puncture the inside wall of the delivery sheath. This advantageously eliminates the need to deliver the repair device in a hard, non-flexible capsule, which makes endoluminal delivery much more difficult. The barbs of this repair device can be placed at alternate levels around the distal end stent so they will not occupy the same space in the collapsed condition. This arrangement allows for a smaller, more flexible delivery system.

The repair device of this invention can also incorporate a biological glue or adhesive on the exterior graft surface around the distal stent to enhance the stability of the connection between the repair device and the migrating stent graft body. The stent graft repair device of this invention can also include a sealing material around the distal stent to enhance sealing between the inside of the migrating stent graft and an external surface of the repair device. This sealing material can be a thin strip of DACRON® felt or it can be a frayed edge or cuff at the edge of the distal stents. These seal enhancing features can also be used around the top portion of the graft material, between the bare stent and the first interior stent to improve sealing between the repair device and the neck of the aneurysm.

The stent graft repair device of this invention can also contain openings or fenestrations to allow blood flow to the renal arteries or other branch arteries. This feature is especially important in cases where the aneurysm has no neck or is extended all the way to the renal arteries. With holes or cut out areas in the device to accommodate branch arteries, the top of the covered section could be placed even more proximal in the aorta.

DETAILED DESCRIPTION

Figure 5A:
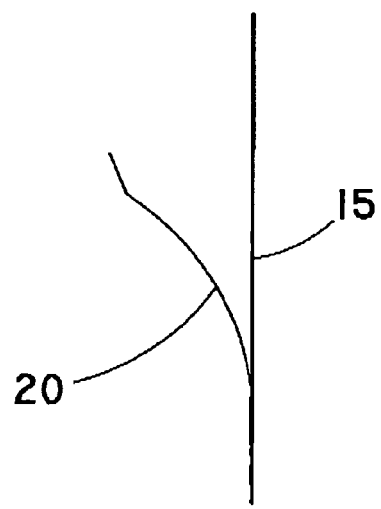
FIG. 5A depicts an enlarged detail of the distal barb as used in this invention.
Figure 5B:
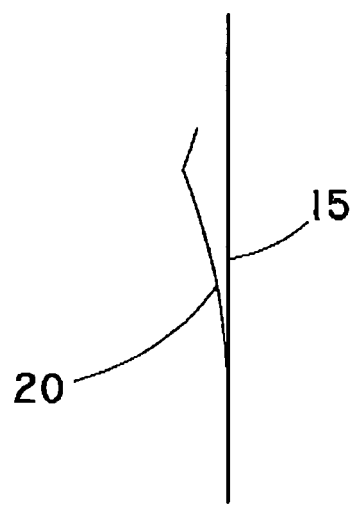
FIG. 5B depicts an enlarged detail of the barb of FIG. 5A with the barb shaped so that when it is compressed inside the sheath, the point of the barb does not engage the wall of the delivery sheath.

The stent graft repair device of this invention can be delivered by a simple commercially available sheath and dilator system (COOK® Incorporated, Bloomington, Ind.) wherein the dilator portion has a recess or indentation to accommodate the compressed device. Delivery can be by percutaneous methods over a guide wire from either above (trans jugular) or from below via the femoral arteries. The low profile, flexible nature of this delivery system, which is made possible in large part by barb 20 as shown in FIGS. 5A and 5B, is ideal for passage through a previously placed stent graft. The lack of ledges or joints as would be the case with a hard capsule, minimizes the chance that the delivery system will catch or tangle with the stents or graft material of the previously placed stent graft. This device could also be delivered in a delivery system similar to the H&LB One Shot delivery system as used for the ZENITH® AAA stent graft as commercially available from Cook Incorporated, Bloomington, Ind. This delivery system makes it possible to release the more distal sections of the device before releasing the proximal, anchoring section. This is possible by the use of a capsule at the proximal end of the sheath that encapsulates the anchoring stent separately from the delivery sheath. The distal sections can be released, the device position refined, then the capsule removed from the top stent, anchoring the device in place. As used herein, proximal means closest to the heart, whereas distal means farthest from the heart.

Figure 1:
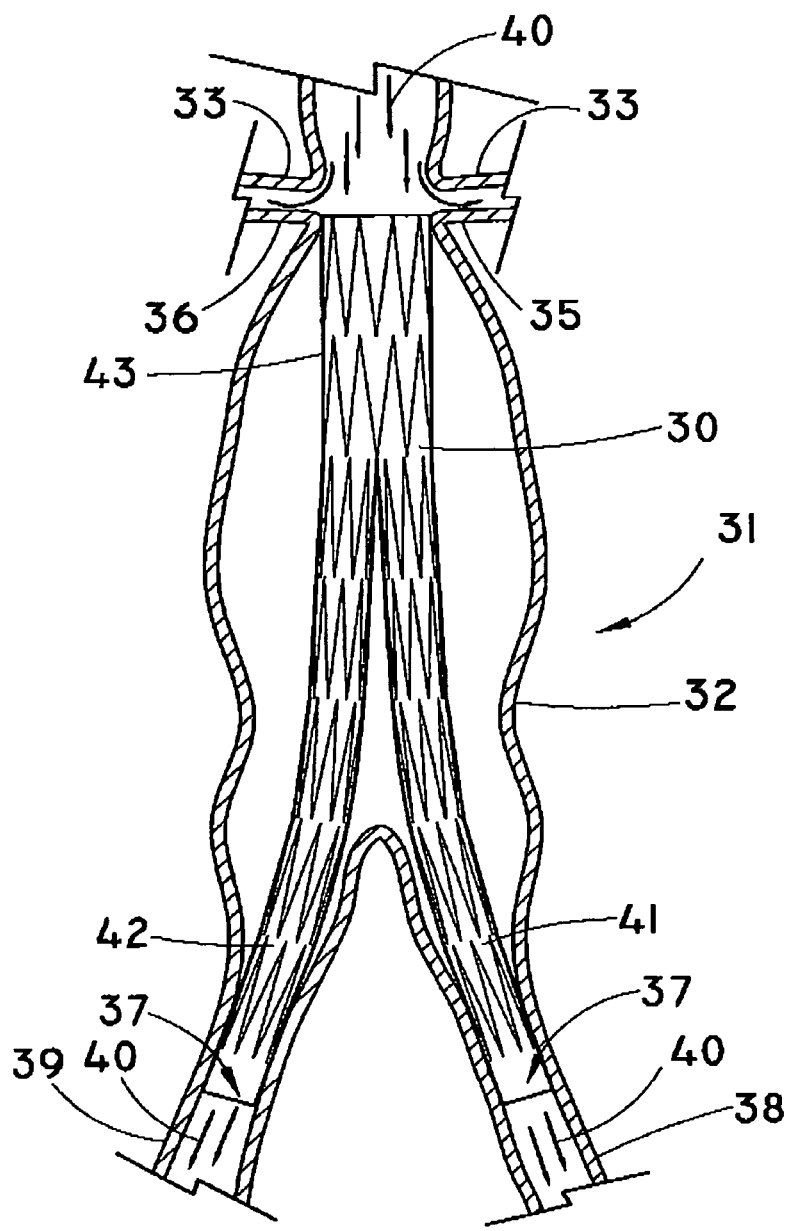
FIG. 1 depicts a typical AAA stent graft in place and functioning in the abdominal aorta. The aneurysm is excluded and protected from blood pressure, and the renal arteries are still receiving blood. The proximal end of the stent is at the origins of the renal arteries and is sealed around a short neck between the aneurysm and renals.

FIG. 1 depicts an abdominal aortic aneurysm (AAA) stent graft 30 implanted in abdominal aorta 31 with proximal end 36 of the stent graft positioned just below the origins of renal arteries 33 and in short neck 35 between the renals and aneurysm 32. Distal ends 37 of the bifurcated stent graft are implanted in contralateral and ipsilateral iliac arteries 38 and 39, respectively. Blood flows in the aorta as indicated by arrows 40 down the descending aorta into renal arteries 33 and into proximal end 36 of stent graft 30. Blood flows through stent graft 30 by entering main body portion 43 and into contralateral and ipsilateral iliac branches 41 and 42. Blood exits distal ends 37 of branches 41 and 42 and into contralateral iliac 38 and ipsilateral iliac 39, respectively. As a result, blood is excluded from flowing into aortic aneurysm 32, thereby advantageously preventing the rupture or dissection of the aneurysm. Bifurcated stent graft 30 is typically a well-known bifurcated modular stent graft having a long and a short iliac leg. In a well-known manner, an extension stent graft is positioned into the short leg via the contralateral iliac artery to complete assembly and placement of the bifurcated modular stent graft in the aorta and iliac arteries. When so positioned, blood is excluded from the aneurysm. One bifurcated commercially available modular stent graft is the ZENITH® stent graft available from Cook Incorporated, Bloomington, Ind. When properly positioned, the stent graft excludes blood flow from the aneurysm without any leakage around the exterior of the stent graft. Should such leaks occur, these are commonly referred to as endoleaks.

Figure 2:
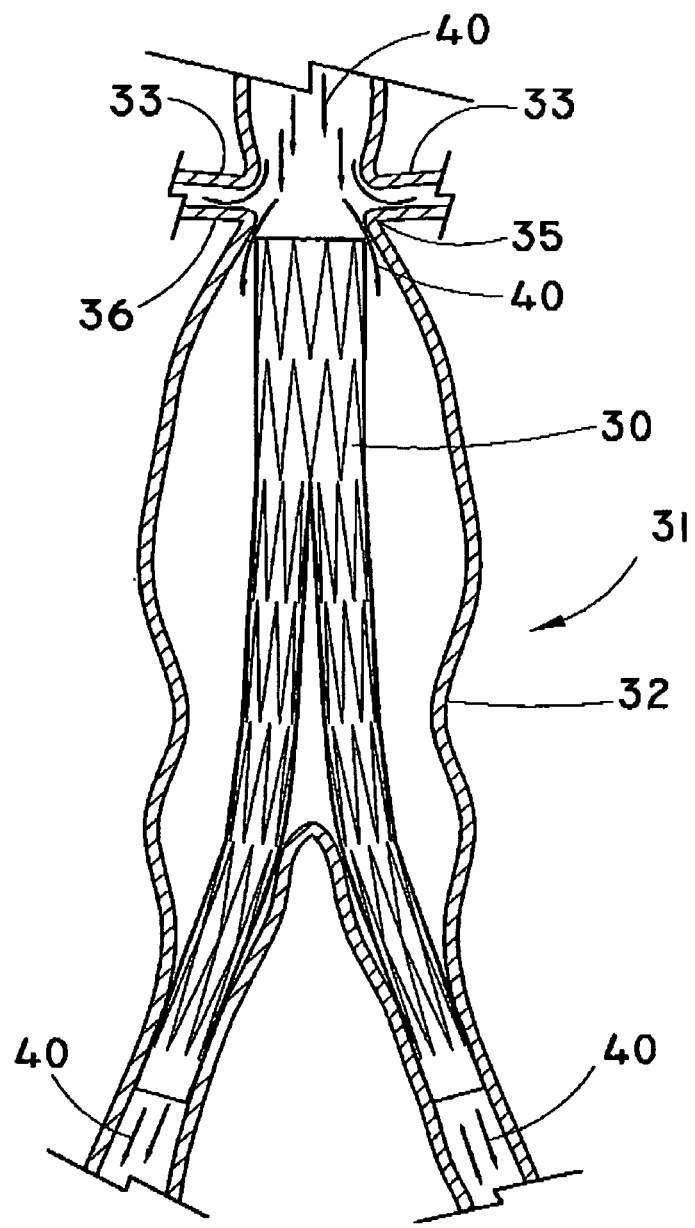
FIG. 2 depicts the stent graft of FIG. 1 after migrating only a few millimeters distally. Blood is once again flowing into the aneurysm, returning to the danger of aneurysm rupture.

FIG. 2 depicts stent graft 30 of FIG. 1 after the proximal end 36 has migrated distally from short aortic neck 35 and the origins of renal arteries 33. As a result, blood flow as indicated by arrows 40 can now once again flow into aneurysm 32 thereby exerting pressure on the aneurysm with the possibility of rupture or dissection. Such a condition is not a desired medical condition, and intervention is required to once again exclude blood flowing into aneurysm 32.

Figure 3:
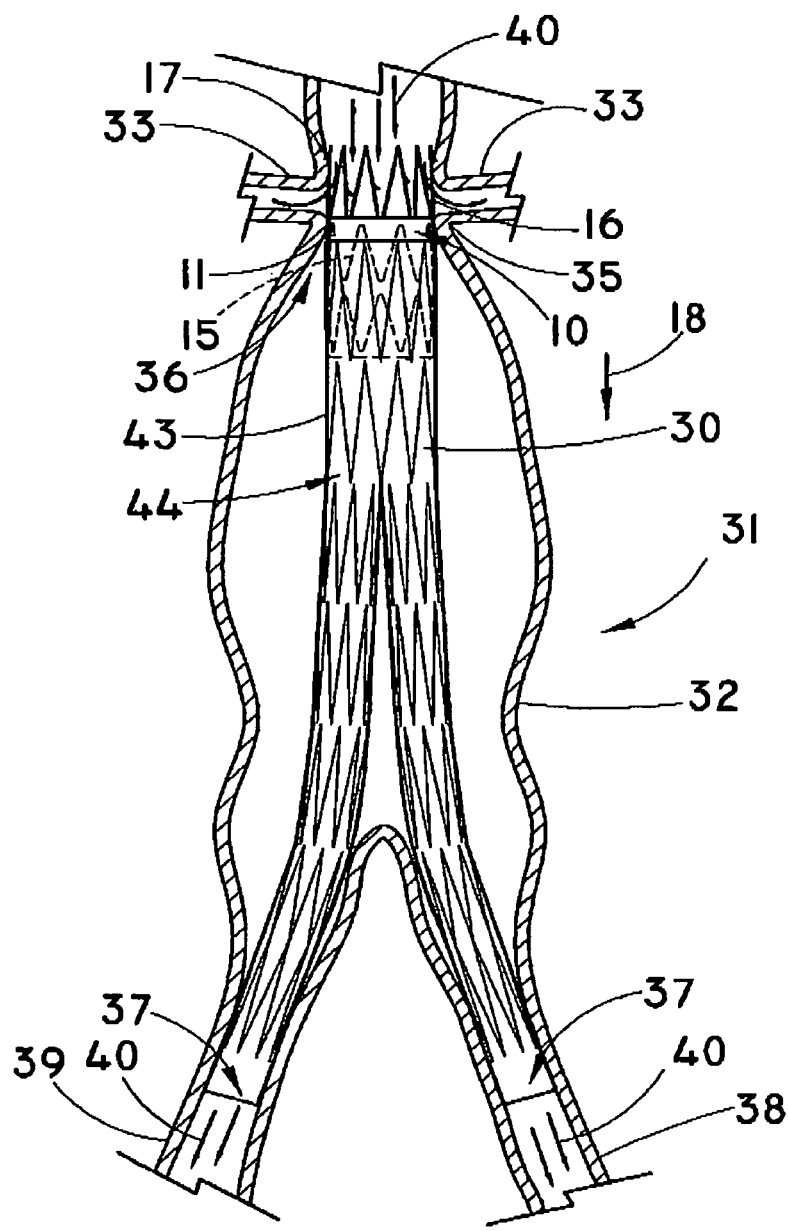
FIG. 3 depicts the repair device of this invention, in place at the top (proximal end) of the stent graft, re-connecting the stent graft to the neck of the aneurysm. The top, bare stent is placed above and across the renals for secure fixation, but blood is still allowed to flow to the renals.

FIG. 3 depicts stent graft 30 of FIG. 2 with illustrative repair device 10 of the present invention positioned in the proximal end of main body 43 of the stent graft. The distal end 13 of the repair device is positioned in the passage of stent graft 30 and conforms to the tubular shape thereof. Repair device 10 includes tubular graft 11 which is positioned just below the origins of renal arteries 33. A bare or uncovered, expandable stent 16 is attached to the proximal end of tubular graft 11 and extends across the ostium of the renal arteries. Included on the struts of bare or uncovered expandable stent 16 is a plurality of barbs 17 pointed in a first downward or distal direction 18 to engage the wall of the aorta. When bare, top expandable stent 16 expands against the wall of the aorta, barbs 17 engage and pierce the aortic wall. As a result, bare or uncovered stent 16 is fixably positioned in the aorta across the ostium of the renals and provides secure attachment of the repair device and the migrated stent graft. Blood, as indicated by arrows 40, continues flow into the renals as well as repair device 10 and stent graft 30.

The repair device also includes a second or interior expandable stent 15 disposed in the passage and on the interior surface of the tubular graft wall of the repair device. This second interior expandable stent pushes the tubular graft against short aortic neck 35 and further provides for the exclusion of blood flow around the repair device as well as the migrated stent graft. Accordingly, blood flows only out the distal end of the branch portions or legs of the stent graft and into the contralateral and ipsilateral iliac arteries 38 and 39, respectively. Blood is once again advantageously excluded from aneurysm sack 32, thereby removing the pressure in the aneurysm sack and allowing it to not expand. Consequently, the excluded aneurysm sack can shrink around exterior surface 44 of the stent graft.

Figure 4:
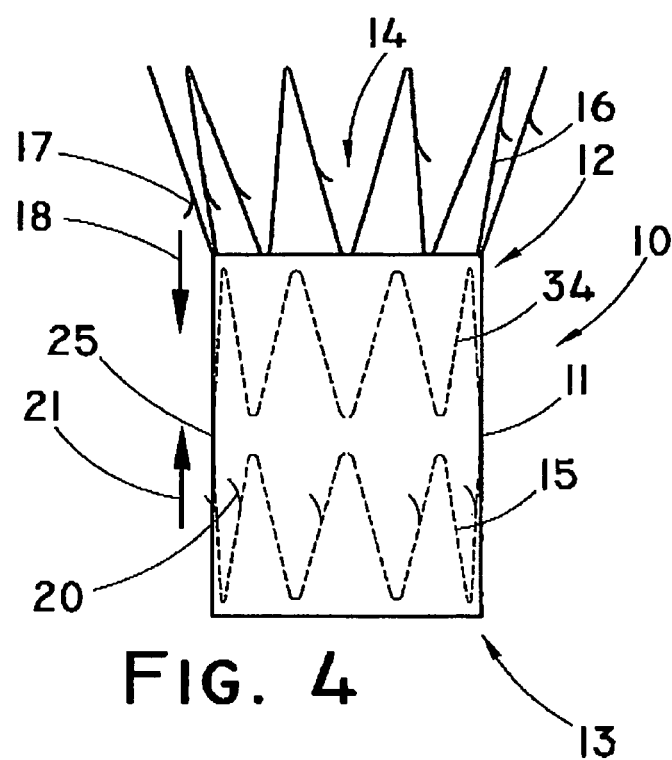
FIG. 4 depicts the stent graft repair device of this invention in the expanded condition. This view depicts a two interior stent repair device with distal barbs. The stents in this embodiment are secured to the inside of the graft material, thus providing a smooth exterior for contact with the inside of the migrating stent graft to be extended.
Figure 7:
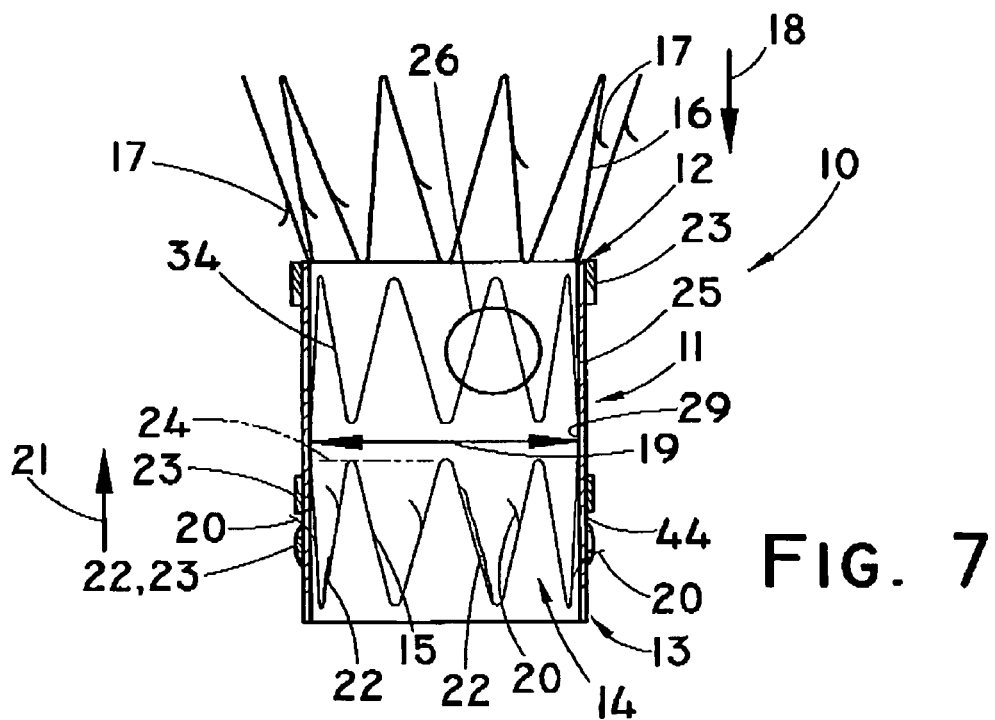
FIG. 7 depicts an enlarged cross-sectional longitudinal view of the stent graft repair device of FIG. 4 and with an optional opening or a fenestration through the graft wall.

FIG. 4 depicts an illustrative embodiment of stent graft repair device 10 of the present invention in an expanded condition. FIG. 7 depicts an enlarged longitudinally cross-sectioned view of the stent graft repair device 10 of FIG. 4 with an opening or fenestration 26 in the tubular graft wall 25. As depicted in FIGS. 4 and 7, stent graft repair device 10 comprises tubular graft 11 having a proximal end 12, a distal end 13 and passage 14 extending longitudinally therethrough. The tubular graft is woven or knitted from a biocompatible material such as a DACRON® material forming a wall 25 with interior surface 29 and exterior surface 44. The graft material can also be any other biocompatible material such as polymers, copolymers, or biological materials. These biological materials can include an extracellular collagen matrix (ECM) material including but not limited to small intestine submucosa (SIS), commercially available from Cook Biotech, West Lafayette, Ind. These biological ECM materials are fully described in detail in the patents of Purdue Research Foundation and Cook Biotech, which are hereinafter identified and incorporated by reference herein. In this particular application of the repair device, tubular graft 11 has a diameter extending across passage 14 and ranges in size from, for example, 15 to 35 mm. The diameter of the tubular graft can be more or less, depending on the size of the vessel in which the repair device is to be implanted. Second interior expandable stent 15 is positioned in passage 14 and on interior surface 29 of tubular graft 11 at distal end 13 thereof. The stent graft repair device can have any number of stents depending on how tall or long the stents are. Typically, two or three stents are utilized, but more stents ranging from four to eight could be utilized if the stents are short. One or more sutures are typically utilized to attach this interior expandable stent to the interior surface or wall of the tubular graft. A plurality of barbs 20 is affixed to this expandable stent and point in a direction 21 toward the proximal end 12 of the tubular graft and repair device. These barbs are utilized to engage the interior surface of the migrating stent graft and secure attachment thereto. Expandable stent 15 is preferably a Gianturco Z stent formed from, for example, stainless steel or other metallic alloys including nickel titanium alloys commercially known as nitinol. These stents can also be formed from any other biological or polymeric material that exhibits resilient properties to expand when released from a compressed condition and press the tubular graft of the repair device against the interior surface of the migrating stent graft, as well as the interior surface of the aortic vessel wall.

Stent graft repair device 10 also includes a bare or uncovered expandable stent 16 attached to the other end of the tubular graft, preferably proximal end 12, and extends longitudinally from passage 14 of the tubular graft. This bare, expandable stent is also of the Gianturco Z stent type and is attached to the proximal end of the tubular graft, using, for example, well-known and commercially available suture material. A plurality of barbs 17 are affixed to the struts of this bare, expandable stent and point in first direction 18 toward the distal end of the tubular graft. The ends or points of barb 17 point toward the distal end of the graft so as to fully engage and pierce the aortic wall when positioned thereagainst. The flow of blood typically flows in first direction 18 and causes barbs 17 to fully engage and insert themselves into the vessel wall. Barbs 20 of the second expandable stent 15 point in a second or proximal direction 21 opposite to that of first direction 18. As previously described, these barbs engage the interior surface of the migrating stent graft to fixedly attach the repair device to the migrating stent graft.

Figure 6:
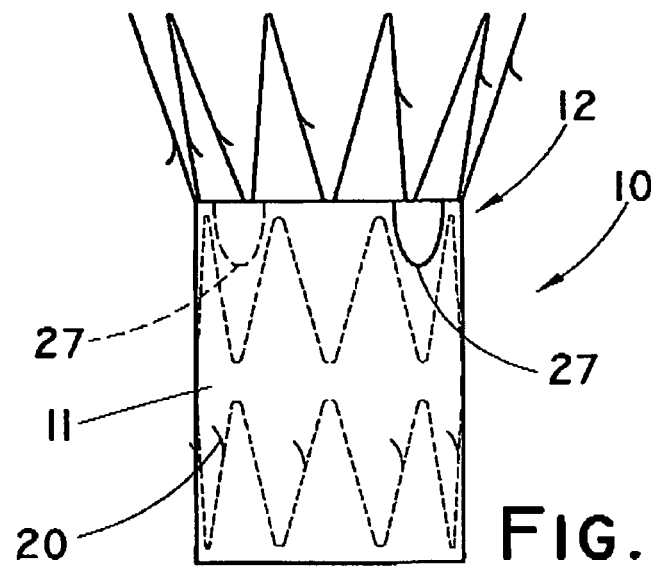
FIG. 6 depicts a stent graft repair device of this invention with a cut out or scallop to allow for blood flow into the renal or other branch arteries.

Depending on the desired length of the tubular graft, which can range from 20 to 60 mm, an additional or second interior expandable stent 34 is disposed on interior surface 29 and in passage 14 of the tubular graft about proximal end 12 thereof. This second interior expandable stent is used in longer length repair devices to expand the tubular graft 11 against hopefully healthy tissue of the aortic wall, typically just below the origins of the renal arteries. However, should healthy tissue not be available to provide a good seal against the vessel wall, the repair device can be moved to a more proximal position above the renal arteries. In such case, tubular graft 11 would preferably include one, preferably two openings or fenestrations 26, in the tubular graft. These openings or fenestrations are positioned directly in front of the origin of the renal arteries so as to permit blood flow into the renal arteries. Preferably two openings or fenestrations would be provided in the tubular graft so as to accommodate both openings of the renal arteries. Should the repair device not be required to fully cover the renal orifices, a cutout or scallop 27 can be formed at, for example, the proximal end 12 of the tubular graft. These cutouts or scallops are positioned about the circumference of the tubular graft to line up with the origins of the renal arteries and allow blood flow to continue into the renal arteries. These cutouts or scallops are depicted in FIG. 6.

FIG. 5A depicts an enlarged view of barb 20 on a strut of stent 15 extending in a radially outward direction to engage, for example, the interior wall of the migrated stent graft. FIG. 5B depicts an enlarged view of barb 20 attached to a strut of stent 15 wherein the barb is pointed radially inward when the stent is positioned in a compressed condition.

Returning to FIGS. 4 and 7, a biological glue 22 can be applied to the surface of the interior expandable stent 15 to enhance the stability between the connection between the repair device and the migrating stent body. The biological glue is commercially available and can also be applied to the exterior surface of the tubular graft to further enhance connection between the repair device and the migrating stent body. A sealing material 23 can also be positioned around the distal expandable stent and on the exterior surface of the tubular graft to enhance the interconnection between the repair device and the stent graft. This sealing material can include a polymer or DACRON® felt. The sealing material can also be a frayed edge or cuff at the edge of the proximal stent. The sealing material 23 can be disposed on the outer surface of the tubular graft and at an edge 24 of the expandable stent. Furthermore, the sealing material can be disposed on the tubular graft between the bare, uncovered stent and the proximal interior stent 34 so as to provide a better seal against the arterial vessel wall.

By way of incorporation by reference herein, the following patents are included for a more detailed description of any and all forms of an ECM or SIS material. These references include U.S. Pat. No. 4,902,508, Tissue Graft Composition; U.S. Pat. No. 4,956,178, Tissue Graft Composition; U.S. Pat. No. 5,275,826, Fluidized Intestinal Submucosa and its Use as an Injectable Tissue Graft; U.S. Pat. No. 5,281,422, Graft For Promoting Autogenous Tissue Growth; U.S. Pat. No. 5,352,463, Tissue Graft for Surgical Reconstruction of a Collagenous Meniscus And Method Therefor; U.S. Pat. No. 5,372,821, Graft for Promoting Autogenous Tissue Growth; U.S. Pat. No. 5,445,833, Tendon or Ligament Graft for Promoting Autogenous Tissue Growth; U.S. Pat. No. 5,516,533, Fluidized Intestinal Submucosa and its Use as an Injectable Tissue Graft; U.S. Pat. No. 5,573,784, Graft for Promoting Autogenous Tissue Growth; U.S. Pat. No. 5,641,518, Method of Repairing Bone Tissue; U.S. Pat. No. 5,645,860, Tissue Graft and Method for Urinary Urothelium Reconstruction Replacement; U.S. Pat. No. 5,695,998, Submucosa as a Growth Substrate for Islet Cells; U.S. Pat. No. 5,711,969, Large Area Submucosal Tissue Graft Constructs; U.S. Pat. No. 5,753,267, Method for Enhancing Functional Properties of Submucosal Tissue Graft Constructs; U.S. Pat. No. 5,755,791, Perforated Submucosal Tissue Graft Constructs; U.S. Pat. No. 5,762,966, Tissue Graft and Method for Urinary Urothelium Reconstruction Replacement; U.S. Pat. No. 5,866,414, Submucosa Gel as a Growth Substrate for Cells; U.S. Pat. No. 5,885,619, Large Area Submucosal Tissue Graft Constructs and Method for Making the Same; U.S. Pat. No. 5,955,110, Multilayered Submucosal Graft Constructs and Method for Making Same; U.S. Pat. No. 5,968,096, Method of Repairing Perforated Submucosal Tissue Graft Constructs; U.S. Pat. No. 5,997,575, Perforated Submucosal Tissue Graft Constructs; U.S. Pat. No. 6,087,157, Device and Method of Analyzing Tumor Cell Invasion of an Extracellular Matrix; U.S. Pat. No. 6,096,347, Myocardial Graft Constructs; U.S. Pat. No. 6,126,686, Artificial Vascular Valves; U.S. Pat. No. 6,187,039, Tubular Submucosal Graft Constructs; U.S. Pat. No. 6,241,981, Composition and Method for Repairing Neurological Tissue; U.S. Pat. No. 6,264,992, Submucosa as a Growth Substrate for Cells; U.S. Pat. No. 6,331,319, Galactosidase Modified Submucosal Tissue; U.S. Pat. No. 6,375,989, Submucosa Extracts; U.S. Pat. No. 6,206,931, Graft Prosthesis Materials; U.S. Pat. No. 6,358,284, Tubular Grafts from Purified Submucosa; U.S. Pat. No. 5,554,389, Urinary Bladder Submucosa Derived Tissue Graft; U.S. Pat. No. 6,099,567, Stomach Submucosa Derived Tissue Graft. In addition, the indicated US and World Intellectual Property Organization patents or publication numbers and the appropriate issue or publication dates are hereby incorporated by reference in their entirety. These additional US and World Intellectual Property Organization publications are as follows: U.S. Pat. No. 6,666,892, Multi-formed Collagenous Biomaterial Medical Device 2003 Dec. 23; US 20030051735A1, Vessel Closure Member, Delivery Apparatus, and Method of Inserting the Member 2003 Mar. 20; WO 03092546A2, Sling for Supporting Tissue 2003 Nov. 13; WO 03092471A2, Cell-Seeded Extracellular Matrix Grafts 2003 Nov. 13; WO 03088844A1, Apparatus and Method for Producing a Reinforced Surgical Staple Line 2003 Oct. 30; WO 03035125A3, Medical Graft Device with Meshed Structure 2003 May 01; WO 03035125A2, Medical Graft Device with Meshed Structure 2003 May 01; WO 03009764A1, Vessel Closure Member and Delivery Apparatus 2003 Feb. 06; WO 03002168A1, Porous Sponge Matrix Medical Devices and Methods 2003 Jan. 09; WO 03002165A1 Graft Prosthesis Devices Containing Renal Capsule Collagen 2003 Jan. 09; WO 0156500A, Implantable Vascular Device 2001 Aug. 09; WO 0154625A1, Stent Valves and Uses of Same 2001 Aug. 02; WO 0110355A1, Tubular Graft Construct 2001 Feb. 15; WO 0032253A1, Radiopaque Implantable Collagenous Biomaterial Device 2000 Jun. 08; WO 0032250A1, A Multi-formed Collagenous Biomaterial Medical Device 2000 Jun. 08 and WO 0032112A1, Embolization Device 2000 Jun. 08. All of the aforementioned references are incorporated by reference herein and may be referred to for detailed descriptions and support for any of the aforementioned embodiments and descriptions of the stent graft repair device and particularly the tubular graft material. It is also contemplated that the bioremodelable substance can be cross-linked as described in the aforementioned references to control the amount of remodeling of tissue coming in proximity to a bioremodelable substance.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 μg/mg, more preferably less than about 2 μg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

Repair device 10 can be delivered to a treatment site using a variety of endovascular techniques. In treating aortic aneurysms, a catheter-based introducer can be used to insert the stent graft repair device into the body through a femoral artery and then into the aorta. The introducer may be similar to those described in WO 03/53761 and in US2002/0198587.

U.S. Pat. No. 5,387,235 entitled "Expandable Transluminal Graft Prosthesis For Repair Of Aneurysm" discloses apparatus and methods of retaining grafts onto deployment devices. These features and other features disclosed in U.S. Pat. No. 5,387,235 could be used with the present invention and the disclosure of U.S. Pat. No. 5,387,235 is herewith incorporated in its entirety into this specification.

U.S. Pat. No. 5,720,776 entitled "Barb and Expandable Transluminal Graft Prosthesis For Repair of Aneurysm" discloses improved barbs with various forms of mechanical attachment to a stent. These features and other features disclosed in U.S. Pat. No. 5,720,776 could be used with the present invention and the disclosure of U.S. Pat. No. 5,720,776 is herewith incorporated in its entirety into this specification.

U.S. Pat. No. 6,206,931 entitled "Graft Prosthesis Materials" discloses graft prosthesis materials and a method for implanting, transplanting, replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herewith incorporated in its entirety into this specification.

PCT Patent Publication No. WO 98/53761 entitled "A Prosthesis And A Method And Means Of Deploying A Prosthesis" discloses an introducer for a prosthesis which retains the prosthesis so that each end can be moved independently. These features and other features disclosed in PCT Patent Publication No. WO 98/53761 could be used with the present invention and the disclosure of PCT Patent Publication No. WO 98/53761 is herewith incorporated in its entirety into this specification.

PCT Patent Publication No. WO 99/29262 entitled "Endoluminal Aortic Stents" discloses a fenestrated prosthesis for placement where there are intersecting arteries. This feature and other features disclosed in PCT Patent Publication No. WO 99/29262 could be used with the present invention and the disclosure of PCT Patent Publication No. WO 99/29262 is herewith incorporated in its entirety into this specification.

PCT Patent Publication No. WO 03/034948 entitled "Prosthesis For Curved Lumens" discloses prostheses with arrangements for bending the prosthesis for placement into curved lumens. This feature and other features disclosed in PCT Patent Publication No. WO 03/034948 could be used with the present invention and the disclosure of PCT Patent Publication No. WO 03/034948 is herewith incorporated in its entirety into this specification.

U.S. Provisional Patent Application Ser. No. 60/392,682, filed Jun. 28, 2002, and U.S. patent application Ser. No. 10/447,406, filed May 29, 2003 and published Dec. 18, 2003 as U.S. Publication No. US2003-0233140, entitled "TriggerWires" disclose release wire systems for the release of stent grafts retained on introducer devices. This feature and other features disclosed in U.S. Provisional Patent Application Ser. No. 60/392,682 and U.S. patent application Ser. No. 10/447,406, filed May 29, 2003 and published Dec. 18, 2003 as U.S. Publication No. US2003-0233140, could be used with the present invention and the disclosure of U.S. Provisional Patent Application Ser. No. 60/392,682 and U.S. patent application Ser. No. 10/447,406, filed May 29, 2003 and published Dec. 18, 2003 as U.S. Publication No. US2003-0233140 are herewith incorporated in their entirety into this specification.

U.S. Provisional Patent Application Ser. No. 60/392,667, filed Jun. 28, 2002, and U.S. patent application Ser. No. 10/609,846, filed Jun. 30, 2003 and published May 20, 2004 as U.S. Publication No. US2004-0098079, entitled "Thoracic Deployment Device" disclose introducer devices adapted for deployment of stent grafts particularly in the thoracic arch. This feature and other features disclosed in U.S. Provisional Patent Application Ser. No. 60/392,667 and U.S. patent application Ser. No. 10/609,846, filed Jun. 30, 2003 and published May 20, 2004 as U.S. Publication No. US2004-0098079, could be used with the present invention and the disclosure of U.S. Provisional Patent Application Ser. No. 60/392,667 and U.S. patent application Ser. No. 10/609,846, filed Jun. 30, 2003 and published May 20, 2004 as U.S. Publication No. US2004-0098079, are herewith incorporated in their entirety into this specification.

U.S. Provisional Patent Application Ser. No. 60/392,599, filed Jun. 28, 2002, and U.S. patent application Ser. No. 10/609,835, filed Jun. 30, 2003 and published Jun. 3, 2004 as U.S. Publication No. US2004-0106978, entitled "Thoracic Aortic Aneurysm Stent Graft" disclose stent grafts that are useful in treating aortic aneurysms particularly in the thoracic arch. This feature and other features disclosed in U.S. Provisional Patent Application Ser. No 60/392,599 and U.S. patent application Ser. No. 10/609,835, filed Jun. 30, 2003 and published Jun. 3, 2004 as U.S. Publication No. US2004-0106978 could be used with the present invention, and the disclosure are herewith incorporated in their entirety into this specification.

U.S. Provisional Patent Application Ser. No. 60/391,737, filed Jun. 26, 2002, U.S. patent application Ser. No. 10/602,930, filed Jun. 24, 2003 and published Mar. 18, 2004 as U.S. Publication No. US2004-0054396, and PCT Patent Publication Number WO 2004/002365 entitled "Stent-Graft Fastening" disclose arrangements for fastening stents onto grafts particularly for exposed stents. This feature and other features disclosed in U.S. Provisional Patent Application No. 60/391,737, U.S. patent application Ser. No. 10/602,930, and PCT Patent Publication No. WO 2004/002365 could be used with the present invention and the disclosure of U.S. Provisional Patent Application Ser. No. 60/391,73, U.S. patent application Ser. No. 10/602,930, and PCT Patent Publication No. WO 2004/002365 are herewith incorporated in its entirety into this specification.

U.S. Provisional Patent Application Ser. No. 60/405,367, filed Aug. 23, 2002, U.S. patent application Ser. No. 10/647,642, filed Aug. 25, 2003 and published Apr. 15, 2004 as U.S. Publication No. US2004-0073289, and PCT Patent Publication No. WO 2004/017868 entitled "Asymmetric Stent Graft Attachment" disclose retention arrangements for retaining onto and releasing prostheses from introducer devices. This feature and other features disclosed in U.S. Provisional Patent Application Ser. No. 60/405,367, filed Aug. 23, 2002, U.S. patent application Ser. No. 10/647,642, filed Aug. 25, 2003 and published Apr. 15, 2004 as U.S. Publication No. US2004-0073289, and PCT Patent Publication No. WO 2004/017868 could be used with the present invention and the disclosure of U.S. Provisional Patent Application Ser. No. 60/405,367, filed Aug. 23, 2002, U.S. patent application Ser. No. 10/647,642, filed Aug. 25, 2003 and published Apr. 15, 2004 as U.S. Publication No. US2004-0073289, and PCT Patent Publication No. WO 2004/017868 are herewith incorporated in its entirety into this specification.

U.S. patent application Ser. No. 10/322,862, filed Dec. 18, 2002 and published as Publication No. US2003-0120332, and PCT Patent Publication No. WO03/053287 entitled "Stent Graft With Improved Adhesion" disclose arrangements on stent grafts for enhancing the adhesion of such stent grafts into walls of vessels in which they are deployed. This feature and other features disclosed in U.S. patent application Ser. No. 10/322,862, filed Dec. 18, 2002 and published as Publication No. US2003-0120332, and PCT Patent Publication No. WO03/053287 could be used with the present invention and the disclosure of U.S. patent application Ser. No. 10/322,862, filed Dec. 18, 2002 and published as Publication No. US2003-0120332, and PCT Patent Publication No. WO03/053287 are herewith incorporated in its entirety into this specification.

U.S. Provisional Patent Application Ser. No. 60/405,769, filed Aug. 23, 2002, U.S. patent application Ser. No. 10/645,095, filed Aug. 23, 2003 and published Apr. 28, 2004 as U.S. Publication No. US2004-0082990, and PCT Patent Publication Number WO 2004/017867 entitled "Composite Prostheses" discloses prostheses or stent grafts suitable for endoluminal deployment. These prostheses and other features disclosed in U.S. Provisional Patent Application Ser. No. 60/405,769, filed Aug. 23, 2002, U.S. patent application Ser. No. 10/645,095, filed Aug. 23, 2003 and published Apr. 28, 2004 as U.S. Publication No. US2004-0082990, and PCT Patent Publication No. WO 2004/017867, could be used with the present invention and the disclosure of U.S. Provisional Patent Application Ser. No. 60/405,769, filed Aug. 23, 2002, U.S. patent application Ser. No. 10/645,095, filed Aug. 23, 2003 and published Apr. 28, 2004 as U.S. Publication No. US2004-0082990, and PCT Patent Publication Number WO 2004/017867 are herewith incorporated in its entirety into this specification.

To help identify elements of the embodiments of the present invention, the following list of element numbers and descriptors are provided. This list does not limit the invention in any manner and is only provided as a convenience for the reader.

LIST OF ELEMENTS

10 Repair device
11 Tubular graft of 10
12 Proximal end of 10
13 Distal end of 10
14 Passageway of 10
15 Interior expandable stent of 10
16 Bare, expandable stent of 10
17 Plurality of barbs on 16

18 Distal direction of 17
19 Diameter of 11
20 Barbs (plurality)
21 Direction (proximal) of 20
22 Biological glue
23 Sealing material
24 Edge of 15
25 Wall of 10
26 Fenestrations in 11
27 Cutout or scallop
28 End of 25
29 Interior surface of 25
30 Stent graft
31 Abdominal aorta
32 Aneurysm of 31
33 Renal arteries
34 Second expandable stent
35 Short neck of 31
36 Proximal end of 30
37 Distal ends of 30
38 Contralateral iliac arteries
39 ipsilateral iliac arteries
40 Blood flow arrows
41 Contralateral iliac branch of 30
42 Ipsilateral iliac branch of 30
43 Main body portion of 30
44 Exterior surface of 30

The invention claimed is:

1. A stent graft repair device, for repairing a pre-existing stent graft in a body vessel, comprising:
a tubular graft of biocompatible graft material having a proximal end, a distal end and; a passage extending longitudinally therethrough
a first expandable stent at the proximal end of the tubular graft and extending beyond the graft material at the proximal end;
the first expandable stent having a first plurality of barbs attached thereto and extending longitudinally therealong and pointing in a direction toward the distal end of the tubular graft, wherein the barbs extend beyong the proximal end of the graft material, and
a second expandable stent disposed on an interior surface of the tubular graft and within the passage of the tubular graft, the second expandable stent having a second plurality of barbs attached thereto and extending longitudinally therealong and pointing in a direction toward the proximal end of the tubular graft, wherein the second plurality of barbs protrude through the tubular graft and are configured to engage graft material at a proximal end of the pre-existing stent graft.

2. The stent graft repair device of claim 1, wherein the tubular graft has a diameter extending across the passage and ranging in size from 15 to 35 millimeters.

3. The stent graft repair device of claim 1, wherein the second plurality of barbs points radially inwardly when the repair device is in a compressed condition.

4. The stent graft repair device of claim 1, further comprising a biological glue on a surface of the second expandable stent.

5. The stent graft repair device of claim 1, further comprising a sealing material around the second expandable stent.

6. The stent graft repair device of claim 5, wherein the sealing material comprises at least one of a polymer felt, a frayed edge, and a cuff.

7. The stent graft repair device of claim 5, wherein the sealing material is disposed at an edge of the second expandable stent.

8. The stent graft repair device of claim 1, further comprising a sealing material disposed on the tubular graft and between the first and the second expandable stents.

9. The stent graft repair device of claim 1, further comprising a third expandable stent disposed on the interior surface and in the passage of the tubular graft.

10. The stent graft repair device of claim 1, wherein the second plurality of barbs are staggered longitudinally around the second expandable stent.

11. The stent graft repair device of claim 1, wherein the tubular graft includes a wall and at least one opening or fenestration extending through the wall.

12. The stent graft repair device of claim 1, wherein the tubular graft includes a wall and at least one cut out or scallop at an end of the wall.

13. A stent graft repair device for repairing a pre-existing stent graft previously placed in a body vessel, comprising:
a tubular graft having a proximal end, a distal end, and a passage extending longitudinally therethrough;
a first expandable stent at a first one of the distal and the proximal ends of the tubular graft and extending beyond the first one of the distal and the proximal ends of the tubular graft, the first expandable stent having a first plurality of barbs attached thereto and extending longitudinally therealong and pointing in a first direction toward the other end of the at least one of the distal and the proximal ends of the tubular graft, wherein the barbs extend beyond the first one of the distal and proximal ends of sthe qraft, and
a second expandable stent disposed on an interior surface and within the passage of the tubular graft, and having a second plurality of barbs attached thereto and extending longitudinally therealong and pointing in a direction toward the first one of the distal and proximal ends of the tubular graft,
wherein the tubular graft includes a wall with an aperture at or adjacent first one of the distal and the proximal ends of the tubular graft, and
wherein the second plurality of barbs protrude through the tubular graft and are configured to engage an internal surface of the pre-existing graft at an end of the pre-existing stent graft.

14. The stent graft repair device of claim 13, wherein the tubular graft has a diameter extending across the passage and ranging in size from 15 to 35 millimeters.

15. The stent graft repair device of claim 13, wherein the second plurality of barbs points towards said passage when the repair device is in a compressed condition.

16. A stent graft repair device for repairing a pre-existing stent graft previously placed in a body vessel,
a tubular graft having a proximal end, a distal end, and a passage extending longitudinally therethrough,
a first expandable stent at a first one of the distal and the proximal ends of the tubular graft and extending beyond the first one of the distal and the proximal ends of the tubular graft, the first expandable stent having a first plurality of barbs attached thereto and extending longitudinally therealong and pointing in a first direction toward the other end of the at least one of the distal and the proximal ends of the tubular graft, wherein the barbs extend beyong the first one of the distal and the proximal ends of the tubular graft, and
a second expandable stent disposed on an interior surface and within the passage of the tubular graft, and having a second plurality of barbs attached thereto and extending longitudinally therealong and pointing in a direction toward the first one of the distal and proximal ends of the tubular graft, and wherein the tubular graft includes a wall with a cut out or scallop at the end of the wall, and wherein the second plurality of barbs protrude through the tubular graft and are configured to engage graft material at the proximal end of the pre-existing stent graft.

17. The stent graft repair device of claim 16, wherein the tubular graft has a diameter extending across the passage and ranging in size from 15 to 35 millimeters.

\* \* \* \* \*

UNITED STATES PATENT AND TRADEMARK OFFICE
CERTIFICATE OF CORRECTION

PATENT NO. : 9,770,320 B2
APPLICATION NO. : 11/578284
DATED : September 26, 2017
INVENTOR(S) : Scott E. Eells et al.

Page 1 of 1

It is certified that error appears in the above-identified patent and that said Letters Patent is hereby corrected as shown below:

In the Claims

In Column 11, Claim 1, Line 42, after "the barbs extend" replace "beyong" with --beyond--.

In Column 12, Claim 16, Line 64, before "the first one of the distal" replace "beyong" with --beyond--.

Signed and Sealed this
Twenty-eighth Day of May, 2019

Andrei Iancu
*Director of the United States Patent and Trademark Office*